United States Patent
Nakamura (10) Patent No.: US 8,299,437 B2
(45) Date of Patent: Oct. 30, 2012

(54) GAMMA RAY DETECTOR AND GAMMA RAY RECONSTRUCTION METHOD

(75) Inventor: Hidehito Nakamura, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 469 days.

(21) Appl. No.: 12/600,216

(22) PCT Filed: May 15, 2007

(86) PCT No.: PCT/JP2007/059973
§ 371 (c)(1),
(2), (4) Date: Nov. 13, 2009

(87) PCT Pub. No.: WO2008/139625
PCT Pub. Date: Nov. 20, 2008

(65) Prior Publication Data
US 2010/0301221 A1    Dec. 2, 2010

(51) Int. Cl.
*G01T 1/20* (2006.01)
(52) U.S. Cl. .................. 250/361 R; 250/370.11
(58) Field of Classification Search .............. 250/361 R, 250/370.11
See application file for complete search history.

(56) References Cited

U.S. PATENT DOCUMENTS

| | | | | |
|---|---|---|---|---|
| 5,412,217 A * | 5/1995 | Miyashita et al. | ....... | 250/390.05 |
| 5,514,870 A * | 5/1996 | Langenbrunner | ............. | 250/367 |
| 5,866,907 A * | 2/1999 | Drukier et al. | ................. | 250/366 |
| 6,459,085 B1 | 10/2002 | Chang et al. | | |
| 2006/0202125 A1* | 9/2006 | Suhami | ......................... | 250/368 |
| 2007/0205369 A1* | 9/2007 | Huth et al. | ..................... | 250/368 |
| 2008/0128631 A1* | 6/2008 | Suhami | ..................... | 250/370.09 |
| 2010/0067001 A1* | 3/2010 | Corbeil et al. | ................. | 356/310 |
| 2010/0308225 A1* | 12/2010 | Nakamura | ................ | 250/361 R |
| 2011/0127435 A1* | 6/2011 | Nakamura | ..................... | 250/362 |

FOREIGN PATENT DOCUMENTS

JP      07-311270      11/1995
(Continued)

OTHER PUBLICATIONS

Suzuki et al. "Performance of Prototype Hard X-ray Polarimeter Utilizing Compton Scattering." Japanese Journal of Applied Physics (45) 1A, 2006, pp. 274-278.*

(Continued)

*Primary Examiner* — David Porta
*Assistant Examiner* — Casey Bryant
(74) *Attorney, Agent, or Firm* — Griffin & Szipl, P.C.

(57) ABSTRACT

Provided are a gamma ray detector and a gamma ray reconstruction method which can be used in SPECT and PET and which combine and reconstruct the information on "Compton-scattered" gamma rays, thereby remarkably increasing gamma ray detection sensitivity, decreasing the amount of a radioactive substance given to a subject, and remarkably reducing the concern about the amount of radiation exposure. The gamma ray detector comprises an absorber scintillator 12 made from an absorptive substance exhibiting a high rate of absorption with respect to gamma rays 1 in an energy region, emitted from a subject, a Compton scattering scintillator 14 made from a Compton scattering substance exhibiting a high probability of Compton scattering, and an energy detector 16 which combines the amounts of gamma ray energy absorption simultaneously measured by the two types of scintillators to reconstruct the gamma rays emitted from the subject. The two types of scintillators 12 and 14 are arranged in multiple layers so as to absorb or Compton-scatter the whole energy of the gamma rays 1.

10 Claims, 9 Drawing Sheets

FOREIGN PATENT DOCUMENTS

| | | |
|---|---|---|
| JP | 2001-159682 | 6/2001 |
| JP | 2007-071858 A | 3/2007 |

OTHER PUBLICATIONS

International Search Report, issued in corresponding application No. PCT/JP2007/059973, completed Jun. 4, 2007, mailed Jun. 12, 2007.

The Science and Technology Foundation of Japan no ' Kenkyu Josei' o Kenkyu Kibanbu no Nakamura Hidehito San ga Sainensho de Saitaku, National Institute of Radiological Sciences News, Jan. 1, 2007, vol. 122, p. 3.

NIST XCOM: Photon Cross Sections Database at http://www.nist.gov/pml/data/xcom/index.cfm/ (last updated Dec. 9, 2011).

* cited by examiner

GAMMA RAY DETECTOR AND GAMMA RAY RECONSTRUCTION METHOD

This is a National Phase Application in the United States of International Patent Application No. PCT/JP2007/059973 filed May 15, 2007. The entire disclosure of the above patent application is hereby incorporated by reference.

BACKGROUND OF THE INVENTION

1. Technical Field of the Invention

The present invention relates to a nuclear medicine diagnosis equipment, and particularly, to a gamma ray detector and a gamma ray reconstruction method for use in SPECT and PET.

2. Description of the Related Art

The gamma ray detector is a radiation detector and is an equipment used in nuclear medicine diagnosis for measuring gamma rays (γ rays) emitted from radioactive medicines given to a patient.

A conventional radiation detector is a laminate of a collimator, a NaI (sodium iodide) and a PMT (photomultiplier tube), in which a lead collimator with parallel micro-pores allows only gamma rays coming from the direction of the pores to reach single crystals of the NaI, whereby fluorescent light is emitted proportional to the amount of gamma ray energy deposited therein, and the PMT detects the light to detect the intensity and the position of the gamma rays.

SPECT is an abbreviation for single photon ECT (ECT stands for emission computed tomography), and is an equipment that creates scintigrams (detection images of a radiation detector) from the directions surrounding a patient using single photon nuclides, thereby obtaining the cross-sectional distribution of radioactive medicines.

Moreover, PET (positron emission tomography) is an abbreviation for positron ECT and is an equipment that uses radioisotopes emitting positrons during decays to successively detect two photons flying out in opposite directions when the positrons combine with electrons, using two detectors, thereby calculating the incidence direction of gamma rays and creating tomographic images.

In relation to the above-described radiation detector used in SPECT and PET, proposals have already been made, for example, in Patent Documents 1 and 2.

The invention of Patent Document 1 provides a universal SPECT/PET equipment that improves energy resolution without decreasing radiation collecting efficiency or spatial resolution, thereby improving the performance as SPECT equipment while maintaining the performance as PET equipment.

Figure 1:
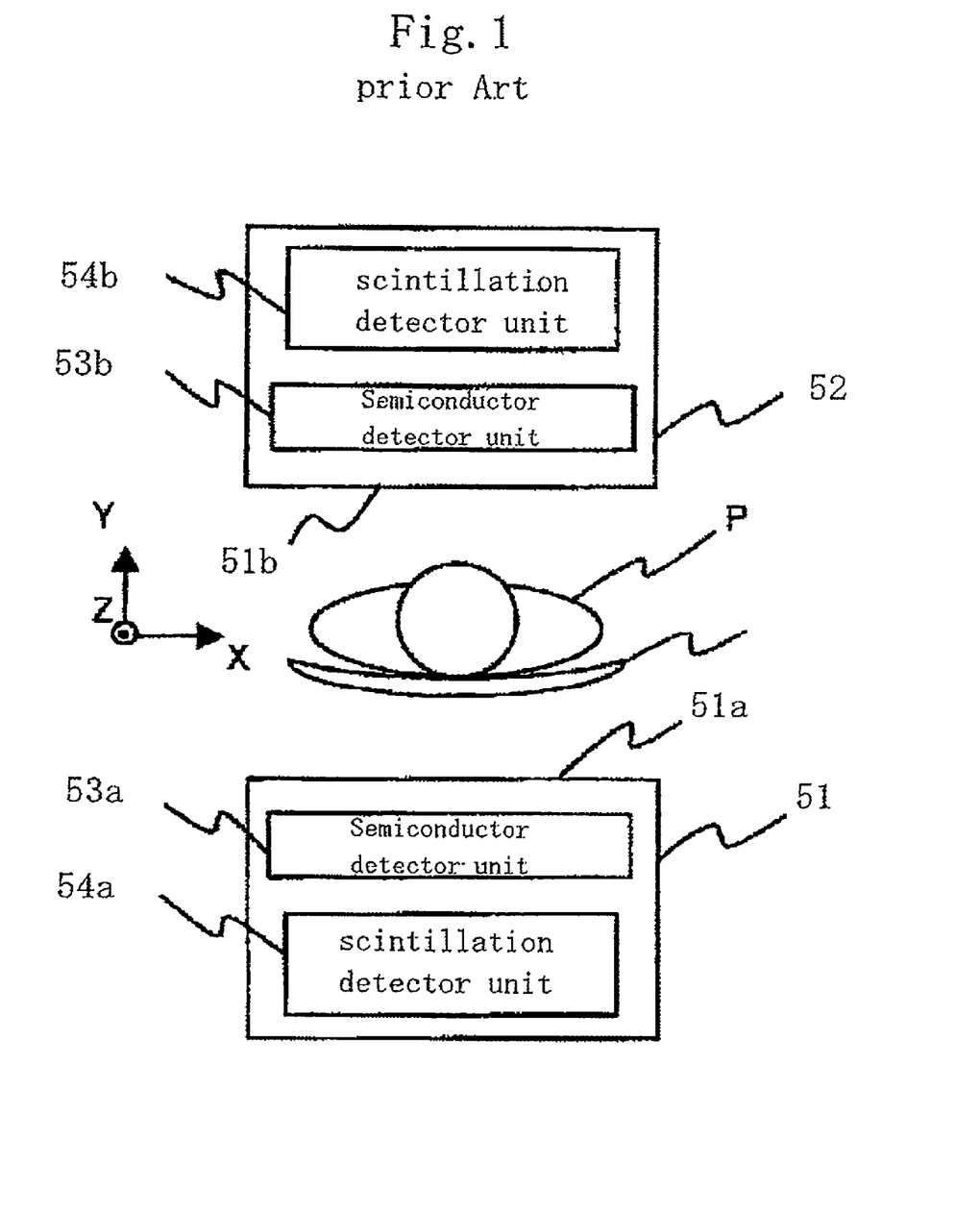
FIG. 1 is a configuration diagram of the equipment described in Patent Document 1.

For this purpose, in the above invention, as illustrated in FIG. 1, radiation detectors 51 and 52 are respectively provided with semiconductor detector units 53a and 53b which are disposed close to radiation incidence surfaces 51a and 52a so as to absorb and detect gamma ray emission having energy of 140 keV, resulting from single photons, and scintillation detector units 54a and 54b which are disposed on opposite sides to the radiation incidence surfaces 51a and 52a with the semiconductor detector units 53a and 53b disposed between them so as to detect gamma ray emission having energy of 511 keV, resulting from positrons.

The invention of Patent Document 2 provides a radiation detector that improves the spatial resolution of a positron emission tomography (PET) equipment attached with a radiation detector so that sensitivity thereof is not decreased.

Figure 2:
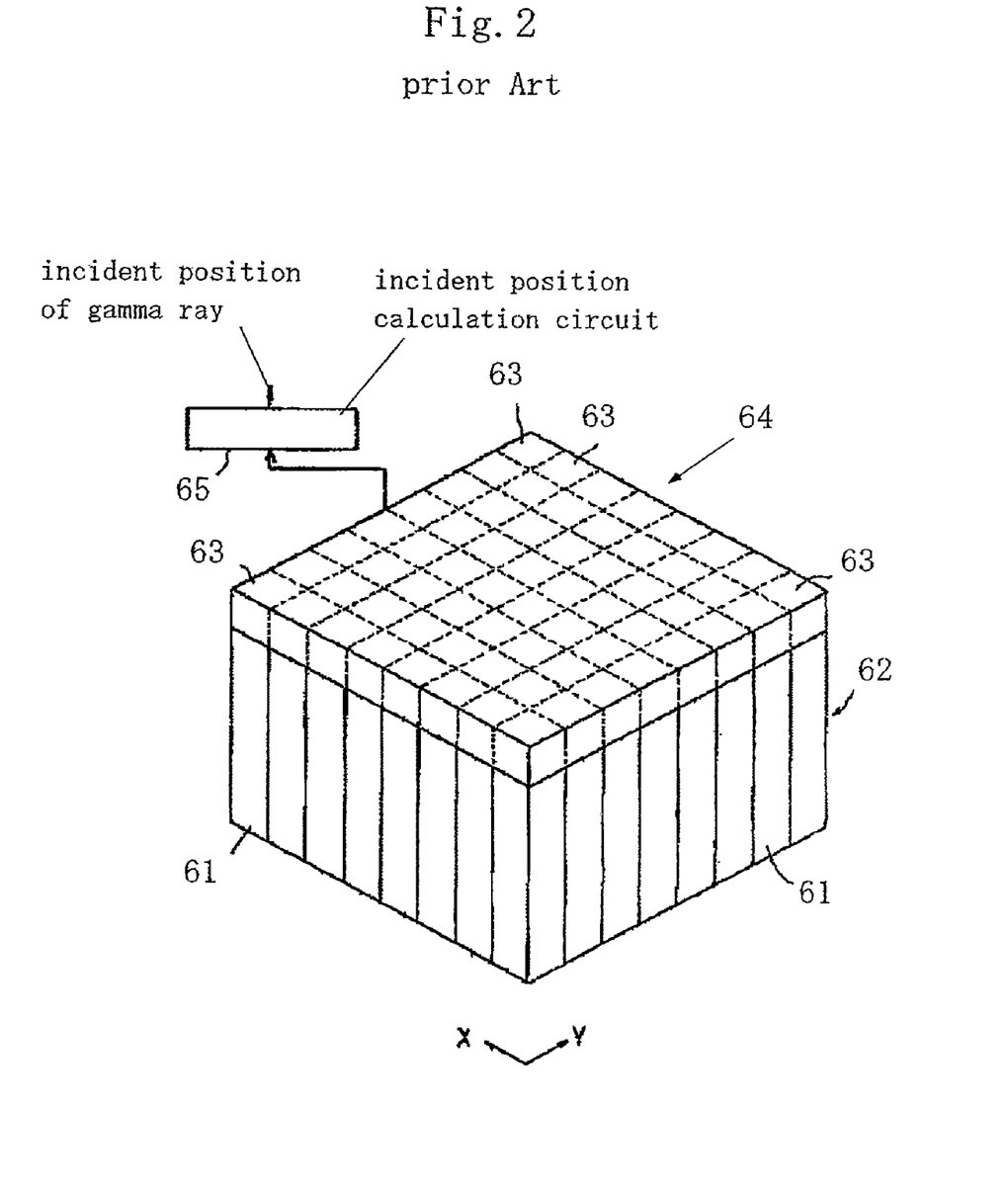
FIG. 2 is a configuration diagram of the detector described in Patent Document 2.

For this purpose, in the above invention, as illustrated in FIG. 2, sixty-four scintillators 61 are closely coupled to construct a scintillator array 62, and respective scintillators 61 are optically coupled to an APD array 64 comprising sixty-eight avalanche photodiodes (APD) 63 which correspond to the scintillators 61 in an one-to-one relation. Gamma rays incident on the scintillator array 62 emit light from scintillators corresponding to the absorbed positions through an interaction, and the emitted light is diffused to neighboring scintillators and the light intensity is detected by the respective APDs 63 of the APD arrays 64. The detection data which are detected by the respective APDs 63 and subjected to photoelectric conversion are input to an incident position calculation circuit 65, whereby the center of the light intensity distribution is calculated based on the respective detection data and then the incident positions of the gamma rays are obtained.

Patent Document 1

Japanese Patent Application Laid-Open No. 2001-159682; "Nuclear Medicine Equipment"

Patent Document 2

Japanese Patent Application Laid-Open No. 7-311270; "Radiation Detector"

The interaction of gamma rays and substance can be broadly divided into "absorption," "Compton scattering," and "electron pair generation;" however, the conventional PET radiation detector has been relying on the "absorption" process to use substances exhibiting a high rate of absorption with respect to gamma rays (e.g., single crystals of NaI, BGO or GSO) in the scintillator in order to identify gamma rays emitted from the human body.

Moreover, in order to increase the amount of gamma rays absorbed by the scintillator, the amount of the radioactive substance given to the subject has to be increased. Therefore, there was a concern that the radiation exposure to the subject may cause problems.

Moreover, although Patent Document 1 describes a universal SPECT/PET equipment having a laminated structure of the semiconductor detector unit and the scintillation detector unit, the respective units were solely used for PET and SPECT, respectively.

Furthermore, in the conventional PET radiation detector, photodiodes are closely arranged on the backside of the scintillator array such as in Patent Document 2 in order to increase the position detection accuracy of gamma rays. However, in order to increase the position detection accuracy with this structure (for example, to a positional accuracy of 1 mm or smaller), too many photodiodes or photomultiplier tubes will be needed, and therefore, the cost will increase and such a laminated structure would be practically impossible to realize.

SUMMARY OF THE INVENTION

The present invention is made to solve the above-described problems. That is to say, a first object of the present invention is to provide a gamma ray detector and a gamma ray reconstruction method which can be used in SPECT and PET and which combine and reconstruct the energy information on "Compton-scattered" gamma rays, which have hitherto been unable to use because the whole gamma ray energy is not deposited to scintillators, thereby remarkably increasing gamma ray detection sensitivity, decreasing the amount of a radioactive substance given to a subject, and remarkably reducing the concern about the amount of radiation exposure.

Owing to these provisions, in cases where the gamma rays exhibit a large energy distribution (e.g., the environmental radiation or the radiation emitted during radiation accidents), the large energy can be detected and hence the identification rate of the emitted gamma rays can be increased, whereby the radiation detector can be used for rapid radiation exposure purposes.

A second object of the present invention is to provide a gamma ray detector and a gamma ray reconstruction method capable of increasing the position detection accuracy of gamma rays at low cost.

In accordance with the present invention, a gamma ray detector is provided which comprises: an absorber scintillator made from an absorptive substance exhibiting a high rate of absorption with respect to gamma rays in an energy region, emitted from a subject; a Compton scattering scintillator made from a Compton scattering substance exhibiting a high probability of Compton scattering with respect to the gamma rays; and an energy detector which combines the amounts of gamma ray energy absorption simultaneously measured by the two types of scintillators to reconstruct the gamma rays emitted from the subject, wherein the two types of scintillators are arranged in multiple layers so as to absorb, or Compton-scatter, the whole energy of the gamma rays.

In accordance with a preferred embodiment of the present invention, the absorber scintillator and the Compton scattering scintillator are arranged alternately or randomly in an identical surface and in the direction of lamination.

The Compton scattering substance is an organic material having a small mass number, consisting of carbon molecules and hydrogen molecules.

Moreover, the energy detector comprises: an absorption light intensity detector which is optically coupled to the absorber scintillator so as to detect the light intensity of the absorber scintillator; a Compton scattering light intensity detector which is optically coupled to the Compton scattering scintillator so as to detect the light intensity of the Compton scattering scintillator; and a calculator which calculates the amount of energy associated with an identical gamma ray from the respective light intensities.

Moreover, the Compton scattering light intensity detector is constructed by a plurality of light intensity detectors which is optically arranged at predetermined intervals on a predetermined surface of the Compton scattering scintillator, and the calculator calculates the incident positions of the gamma rays from the light intensity distribution of the plurality of light intensity detectors.

Moreover, in accordance with the present invention, a gamma ray reconstruction method is provided which comprises: arranging an absorber scintillator and a Compton scattering scintillator in multiple layers so as to absorb, or Compton-scatter, the energy of gamma rays, the absorber scintillator being made from an absorptive substance exhibiting a high rate of absorption with respect to the gamma rays in an energy region, emitted from a subject, and the Compton scattering scintillator being made from a Compton scattering substance exhibiting a high probability of Compton scattering with respect to the gamma rays; and combining the amounts of gamma ray energy absorption simultaneously measured by the two types of scintillators to reconstruct the gamma rays emitted from the subject.

In accordance with a preferred embodiment of the present invention, a plurality of light intensity detectors is optically arranged on a predetermined surface of the Compton scattering scintillator so as to calculate the incident positions of the gamma rays from the light intensity distribution of the plurality of light intensity detectors.

In accordance with the detector and method of the present invention, since the absorber scintillator and the Compton scattering scintillator are arranged in multiple layers so as to absorb, or Compton-scatter, the whole energy of the gamma rays, it is possible to absorb, or Compton-scatter, any of the gamma rays in the energy range where energy is emitted from the subject.

Moreover, since the amounts of gamma ray energy absorption simultaneously measured by the two types of scintillators are combined to reconstruct the gamma rays, it is possible to detect and identify most of the gamma rays emitted from the human body in SPECT and PET.

Therefore, the detector and method of the present invention can be used in SPECT and PET, and the gamma ray detection sensitivity can be increased remarkably. Moreover, in cases where the gamma rays exhibit a large energy distribution, the whole energy can be detected and hence the identification rate of the gamma rays emitted from the human body can be increased.

As a result, the detection sensitivity can be increased and a high gamma ray identification rate can be provided. Therefore, it is possible to remarkably decrease the amount of a radioactive substance given to a subject and to remarkably reduce the concern about the amount of radiation exposure.

In accordance with a preferred embodiment of the present invention, the Compton scattering light intensity detector is constructed by a plurality of light intensity detectors which is optically coupled to a side face of the Compton scattering scintillator. With the use of a plurality of light intensity detectors, the incident positions of the gamma rays can be calculated from the light intensity distribution obtained by the plurality of light intensity detectors. Therefore, in the case of using a scintillator having a gamma ray incidence surface which has a large format (for example, 60 mm×60 mm) compared to the conventional one, a positional accuracy of 1 mm or smaller can be obtained with eight light intensity detectors, for example.

Furthermore, the gamma ray reconstruction method can provide the universality as the basics of a radiation detector used in various fields, for example, environmental radiation physics as well as radiation physics and medical physics.

DESCRIPTION OF THE PREFERRED EMBODIMENT

Preferred embodiments of the present invention will be described hereinbelow with reference to the accompanying drawings. In the respective drawings, the same components or elements will be denoted by the same reference numerals, and the redundant descriptions thereof will be omitted.

In recent years, researches regarding tumor metabolism have been progressed successively from treatment to diagnosis and to prevention. In these researches, vigorous efforts are being made to enable positron labeling agents ($C^{11}$-methionine; FDG) to be used for estimation of tissue energy metabolism. In such researches and inspection, since the positron labeling agents are radioactive substances, a radiation detector capable of reducing the mental burden of a subject to the minimum level and making quick and appropriate determinations becomes of importance. Another problem is related to its popularization, which is how to suppress the increase in radiation exposure to the subject.

(Interaction of Gamma Rays and Substance)

Figure 3A:
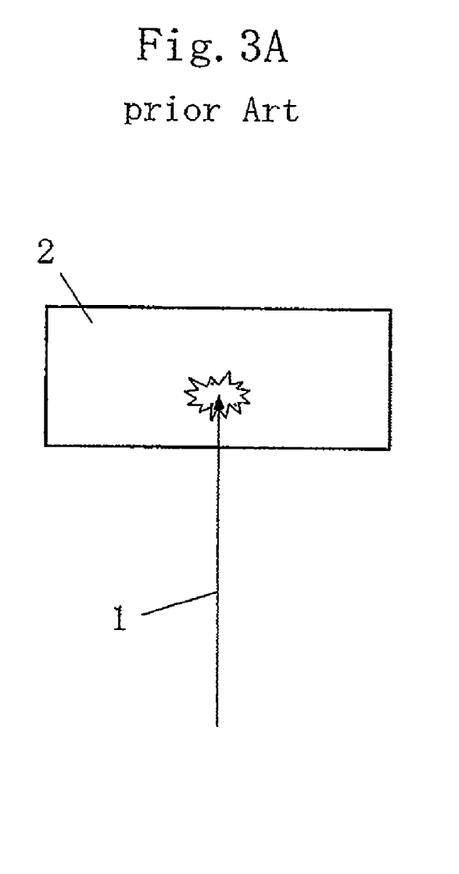
FIG. 3A is a diagram illustrating the interaction of absorption between a gamma ray and a substance.
Figure 3B:
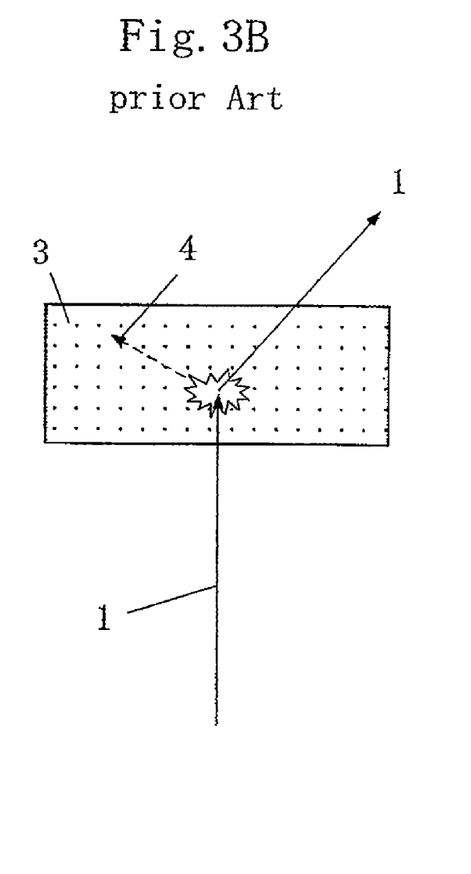
FIG. 3B is a diagram illustrating the interaction of Compton scattering between a gamma ray and a substance.

FIGS. 3A and 3B are views illustrating interactions of gamma rays and substance which are of importance for developing a medical detector. FIG. 3A illustrates absorption of gamma rays, in which the gamma ray 1 collides with electrons in a substance 2 and the whole energy is deposited in the substance 2. FIG. 3B illustrates Compton scattering of gamma rays, in which the gamma ray 1 collides with an electron 4 in a substance 3 and a portion of its energy is deposited in the substance 3.

The interaction of gamma rays and substance can be broadly divided into "absorption," "Compton scattering," and "electron pair generation." Considering the gamma ray energy emitted from the agents used in a positron emission tomography (PET) equipment, the processes of importance for developing a medical radiation detector are "absorption" and "Compton scattering" illustrated in FIGS. 3A and 3B, respectively, and the "electron pair generation" process can be ignored.

All SPECT/PET equipments which have been developed up to now are using a radiation detector relying on the "absorption" process. In the "Compton scattering" process (FIG. 3B) where only a portion of the energy of the gamma ray 1 is deposited in the substance (scintillator), the energy of gamma rays detected from the substance 3 is lower than that of the gamma rays emitted from the human body. Since it is difficult to identify whether or not the detected gamma rays are the gamma rays emitted from the human body, the Compton scattering has conventionally been treated as a background source.

However, in the energy region (about 1 MeV region) of the gamma rays 1 emitted from the human body, the dominant process is the Compton scattering (as will be described later, the reaction probability thereof is higher than that of the "absorption" process by one digit or more).

In the present invention, the "Compton scattering" which has hitherto been treated as a background source in the conventional radiation detector is taken into account, thereby remarkably increasing the detection efficiency by making the most of the information on Compton scattering.

Hereinafter, the radiation detector according to the present invention will be referred to as "gamma ray detector" and the detection method according to the present invention will be referred to as "gamma ray reconstruction method."

Figure 4:
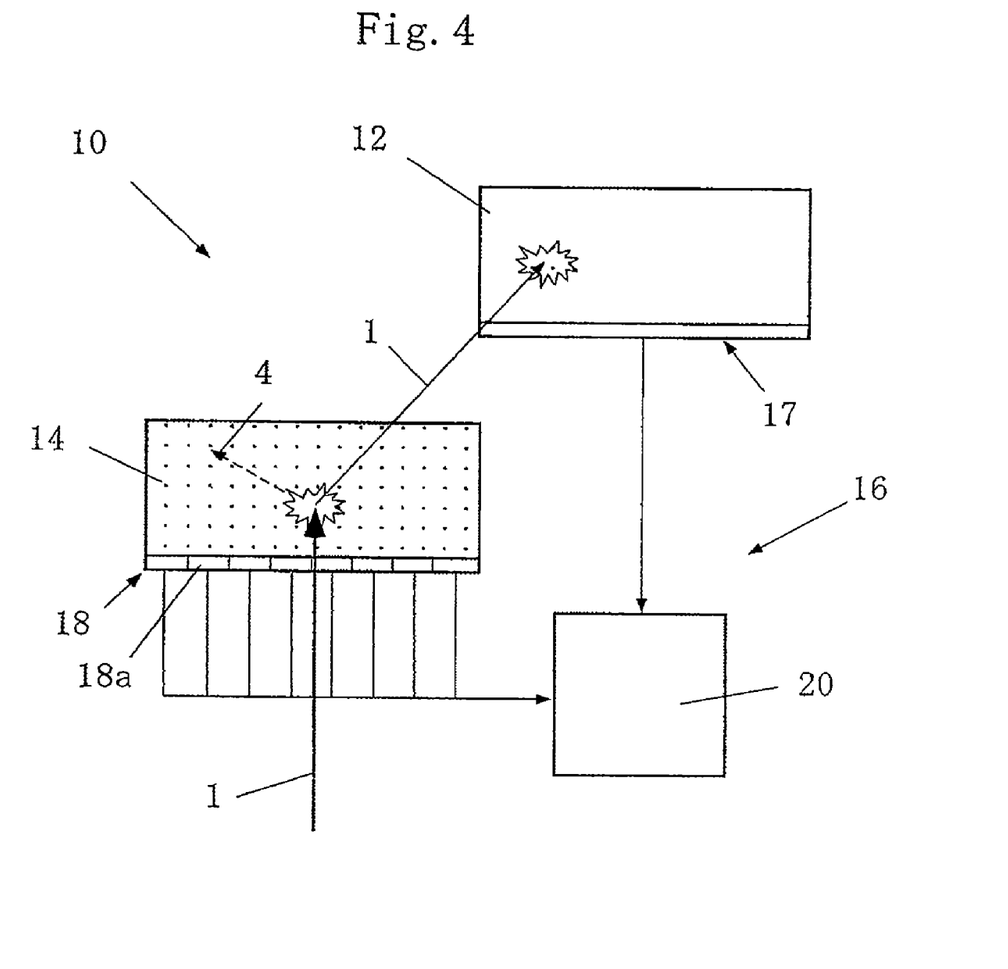
FIG. 4 is a general configuration diagram of a gamma ray detector of the present invention.

FIG. 4 is a general configuration diagram of the gamma ray detector of the present invention.

In the drawing, a gamma ray detector 10 according to the present invention is equipped with an absorber scintillator 12, a Compton scattering scintillator 14, and an energy detector 16.

The absorber scintillator 12 is made from an absorptive substance exhibiting a high rate of absorption with respect to the gamma rays 1 in an energy region, emitted from a subject (for example, the human or animals). The energy region is about 1 MeV, for example.

Figure 9A:
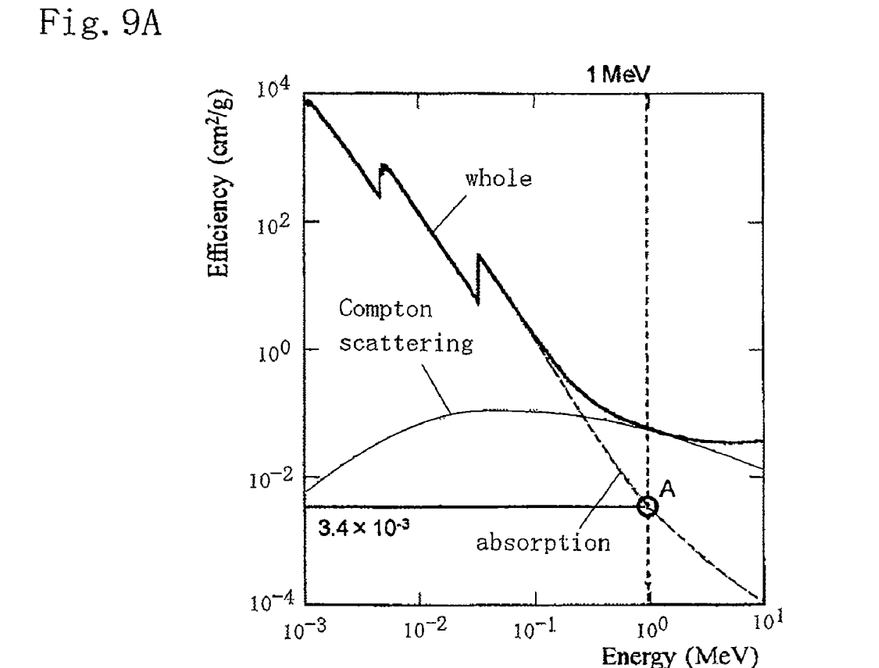
FIG. 9A is a view illustrating the reaction probabilities of gamma rays.

The absorptive substance exhibiting a high rate of absorption with respect to the gamma rays 1 is preferably an inorganic material, such as, for example, NaI (sodium iodide). Referring to FIG. 9A which will be described later, the reaction probability of NaI with respect to gamma rays in 1 MeV energy range is about $3.4 \times 10^{-3}$.

The Compton scattering scintillator 14 is made from a Compton scattering substance exhibiting a high probability of Compton scattering with respect to the gamma rays 1 in the energy region, emitted from the subject.

Figure 9B:
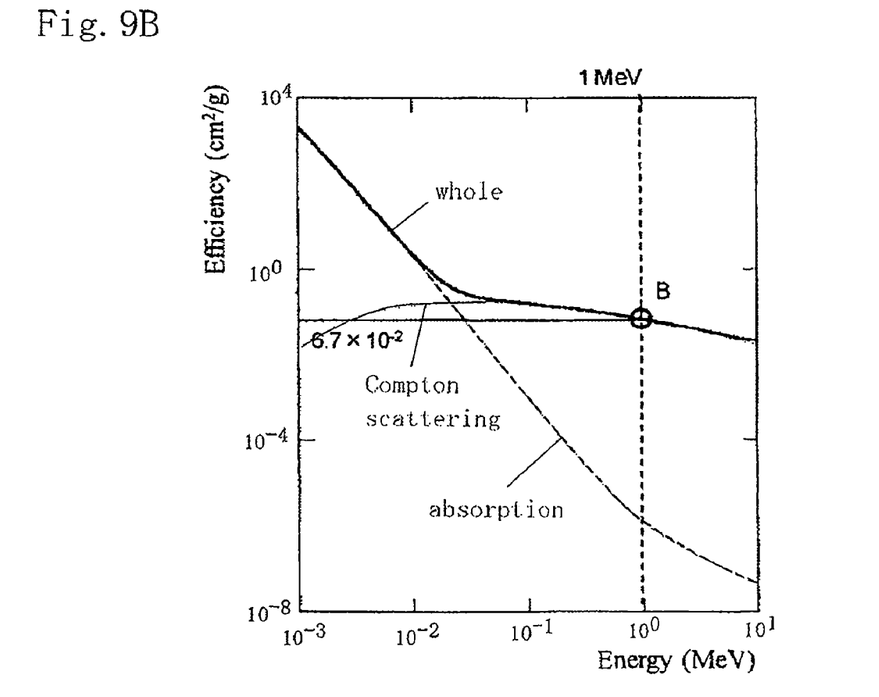
FIG. 9B is another view illustrating the reaction probabilities of gamma rays.

The Compton scattering substance exhibiting a high probability of Compton scattering is preferably an organic material, and particularly preferably is an organic material having a small mass number, consisting of carbon molecules and hydrogen molecules. A plastic scintillator or p-terphenyl is an example of the scintillator of the organic material. Referring to FIG. 9B which will be described later, the reaction probability of the plastic scintillator with respect to the gamma rays in 1 MeV energy range is about $6.7 \times 10^{-2}$.

The above-described two types of scintillators 12 and 14 are arranged in multiple layers (for example, 3 layers) so as to absorb, or Compton-scatter, the whole energy of the gamma rays 1. As will be described later, for better results, the absorber scintillator 12 and the Compton scattering scintillator 14 may be arranged alternately or randomly in an identical surface and in the direction of lamination.

Although FIG. 4 illustrates the case where the gamma rays 1 emitted from the subject interact in the Compton scattering scintillator 14, so that a portion of its energy is absorbed in the Compton scattering scintillator 14 and the remaining Compton scattered energy is absorbed in the absorber scintillator 12, since the absorption in both scintillators occurs simultaneously from the measurement perspective, the measurement is simultaneously performed by the energy detector 16. The energy detector 16 has a function of combining the simultaneously measured amounts of energy absorption of the gamma rays 1 to reconstruct the gamma rays.

In the drawing, the energy detector 16 is constructed by an absorption light intensity detector 17, a Compton scattering light intensity detector 18, and a calculator 20.

The absorption light intensity detector 17 is mounted (optically coupled) on a side face of the absorber scintillator 12 so as to receive light emitted from the absorber scintillator 12 resulting from the absorbed energy of the gamma rays 1, thereby detecting the light intensity of the absorber scintillator 12. In this example, although it has a configuration that the entire light intensities are detected by one absorption light intensity detector 17, the absorption light intensity detector may be configured by a plurality of light intensity detectors.

The Compton scattering light intensity detector 18 is mounted so as to be optically coupled to one or two or more side faces of the Compton scattering scintillator 14 so as to detect the light intensity of the Compton scattering scintillator 14 resulting from the absorbed energy of the gamma rays 1. In this example, the Compton scattering light intensity detector 18 is constructed by a plurality (eight in the drawing) of light intensity detectors 18a which is arranged at regular intervals on one side face (the lower face in the drawing) of the Compton scattering scintillator 14. The Compton scattering light intensity detector 18 and the absorption light intensity detector 17 are photomultiplier tubes or a multi-anode photomultiplier tube or a semiconductor detector comprising a plurality of cells.

The calculator 20 is a computer, for example, which receives the respective light intensities of the absorption light intensity detector 17 and the Compton scattering light intensity detector 18 and performs reconstruction calculation for calculating the total amount of energy from the respective light intensities, assuming that a plurality of coincident inputs, i.e., light intensities, is attributable to identical gamma rays 1.

Moreover, by suppressing the occurring frequency of the gamma rays 1 from the radioactive substance given to the subject low, it is possible to remarkably decrease the amount of the gamma rays 1 simultaneously occurring from different positions. Therefore, the identification of identical gamma rays 1 can be made by determining that the respective light intensities of two or more detectors 17 and 18 detected simultaneously are attributable to the same gamma rays 1.

In this example, the calculator 20 is configured to calculate the incident positions of the gamma rays 1 from the light intensities detected by a plurality of light intensity detectors 18a. The calculation means will be described later.

That is to say, the gamma ray detector 10 of the present invention has such a configuration that by using a plurality of fluorescent screens (scintillators 12 and 14), the simultaneously measured energies, one of Compton electrons scattered on the fluorescent screen (for example, the Compton scattering scintillator 14) where interaction occurs and the other of the scattered gamma rays are combined together to reconstruct the energy of the original gamma rays 1. Owing to such reconstruction, since the respective energies of the gamma rays 1 diffused to the respective scintillators are summed together, the detection counts of the gamma rays are added and hence the detection efficiency can be improved.

Figure 5A:
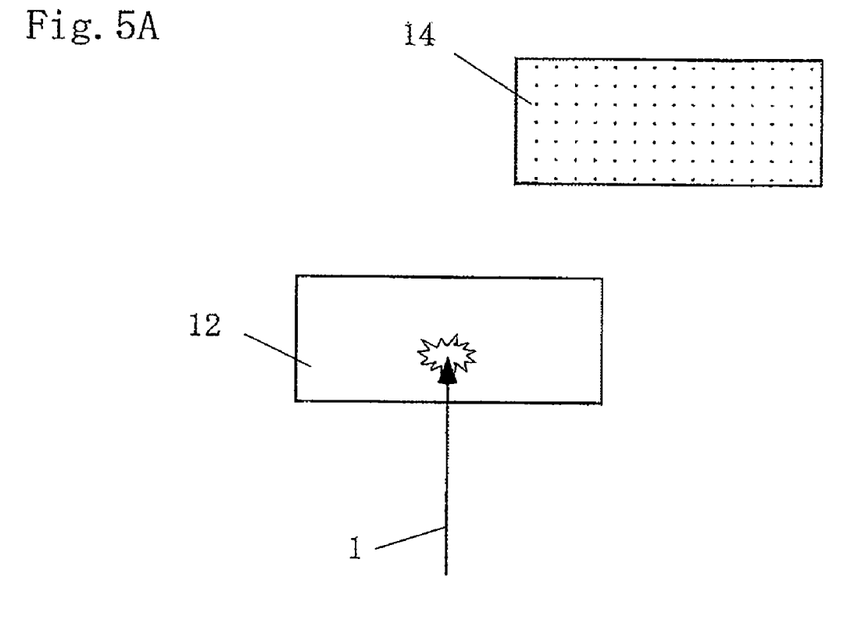
FIG. 5A is a diagram illustrating an absorption process in the present invention.
Figure 5B:
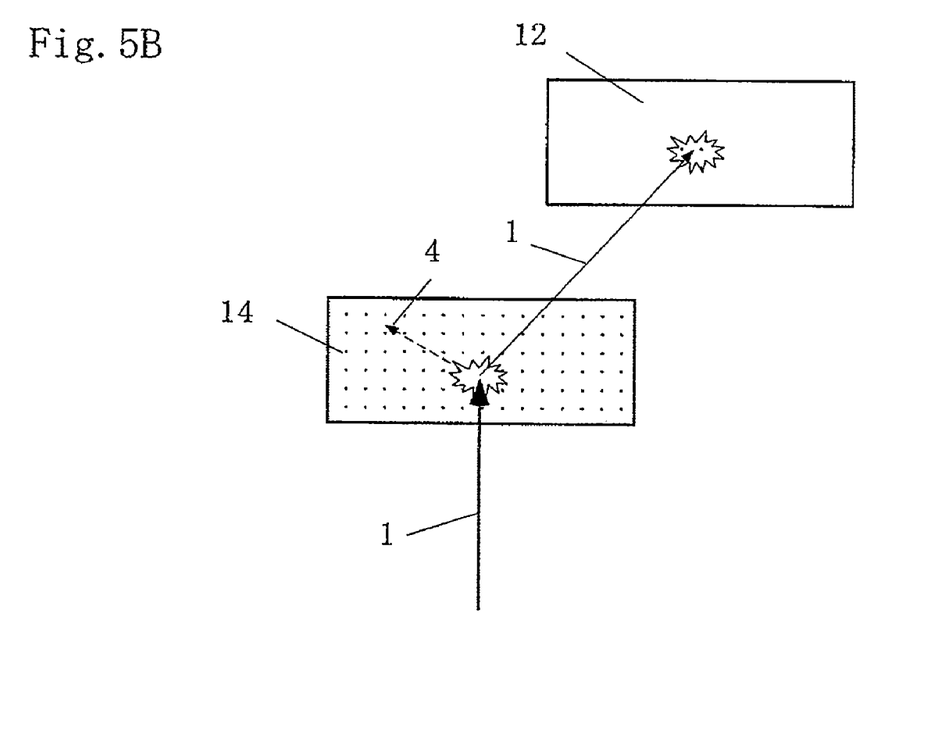
FIG. 5B is a diagram illustrating a Compton scattering process in the present invention.

FIG. 5A is a view illustrating the absorption process in the present invention, and FIG. 5B is a view illustrating the Compton scattering process in the present invention.

As illustrated in FIG. 5A, when a gamma ray 1 is incident on the absorber scintillator 12 and absorbed therein, the detected energy is identical to the energy of the original gamma ray 1, and therefore, the gamma ray can be identified as the gamma ray 1 emitted from the human body.

As illustrated in FIG. 5B, when the gamma ray 1 which is Compton scattered on the Compton scattering scintillator 14 and the gamma ray 1 which is then made incident on the absorber scintillator 12 and absorbed therein are measured simultaneously, the energies of both gamma rays are summed together, whereby the energy of the original gamma ray 1 can be reconstructed.

Similarly, in cases where the Compton scattering occurs more than twice, since the energy of Compton scattered electrons and the energy of the absorbed gamma rays are summed together to reconstruct the energy of the gamma rays 1, the detection count of gamma rays are added together and hence the detection efficiency can be increased.

(Gamma Ray Detector Using Gamma Ray Reconstruction Method)

Figure 6:
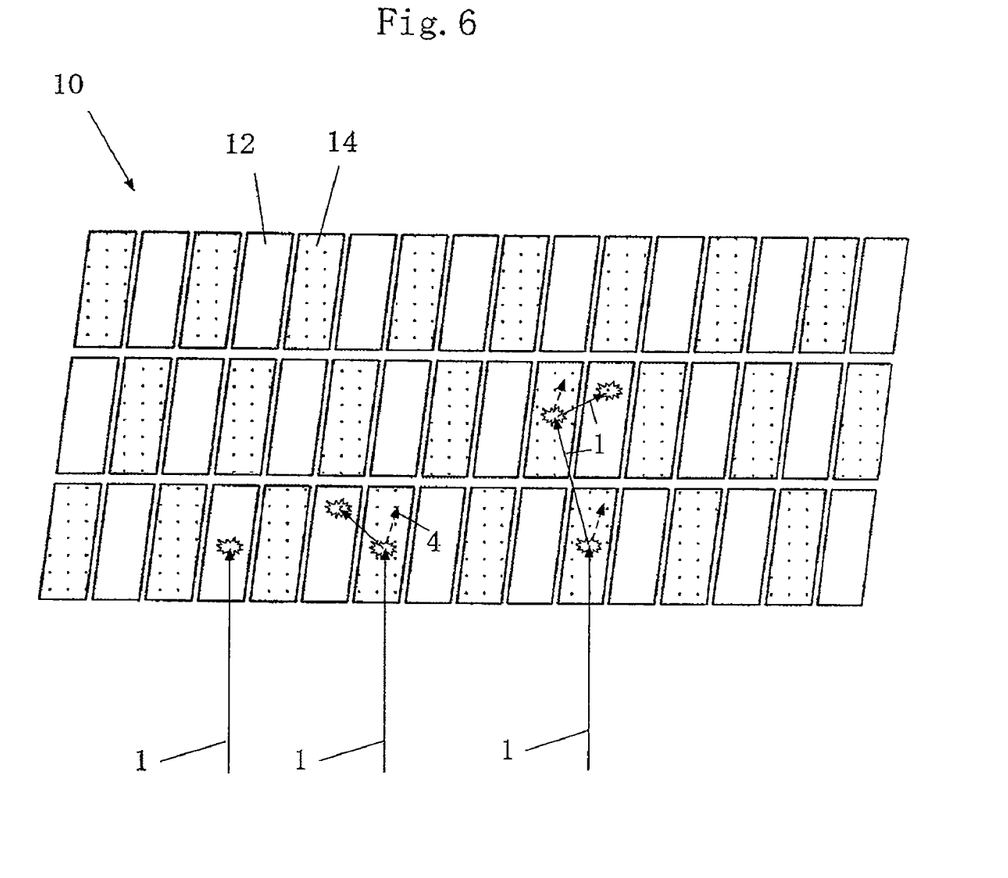
FIG. 6 is a schematic view of the gamma ray detector of the present invention, arranged in multiple layers.

FIG. 6 is a schematic view of the gamma ray detector of the invention which is arranged in multiple layers. In the drawing, the gamma rays 1 are made incident from the bottom, and two types of scintillators constituting the gamma ray detector of the present invention are arranged in three layers with respect to the gamma rays 1 in the thickness direction thereof. Since the multi-layer arrangement can provide a higher probability of interaction between the gamma rays and the scintillators, the detection count of the gamma rays that can be reconstructed can be increased and hence the detection efficiency can be increased.

In this example, the respective scintillators are preferably configured into parallelogram in the thickness-directional cross section rather than having a perfect cubic form. For better results, the angle of the parallelogram with respect to its bottom should be smaller than 90 degrees and equal to or larger than 60 degrees, and the distance where the Compton scattered gamma rays 1 can be absorbed in other neighboring scintillators should be set as long as possible.

In FIG. 6, the above-described two types of scintillators 12 and 14 (hereinafter, referred to simply as "fluorescent screen") are alternately arranged in a layered blind-like structure. The layered blind-like structures are connected using a well-known technique. By combining the plurality of fluorescent screens, the gamma rays 1 are detected. In the drawing, a normal absorption process and the first and second Compton scattering processes are illustrated.

Hitherto, the fluorescent screens (organic scintillators such as plastic scintillators or p-terphenyl) which consist of molecules having a small mass number have not been dealt as medical radiation detectors because they exhibit low sensitivity to gamma ray absorption and superior sensitivity to Compton scattering.

However, the sensitivity to Compton scattering is one digit or more higher than the sensitivity to gamma ray absorption in inorganic scintillators (BGO scintillators or GSO scintillators) which are often used as the PET detectors (in the later-described example of FIGS. 9A and 9B, it is of about $6.7 \times 10^{-2}$ compared to that of about $3.4 \times 10^{-2}$).

Therefore, in the present invention, in order to utilize both sensitivities to absorption and Compton scattering, rather than only to increase the sensitivity to gamma ray absorption to improve the detector sensitivity, the detector is configured to have such a layered blind-like structure having a plurality of types (organic and inorganic) fluorescent screens arranged geometrically.

Referring to FIG. 5B, since the gamma rays have already had a portion of its energy deposited in the Compton scattering scintillator 14, they are easily absorbed later in the absorber scintillator 12. This is because the absorption rate of gamma rays on the scintillators depends on its energy. Therefore, compared to the case where only the absorber scintillator 12 are arranged in multiple layers, by incorporating the Compton scattering scintillator 14 as in the present invention, it is possible to detect energy close to the energy of the original gamma rays 1.

Figure 7:
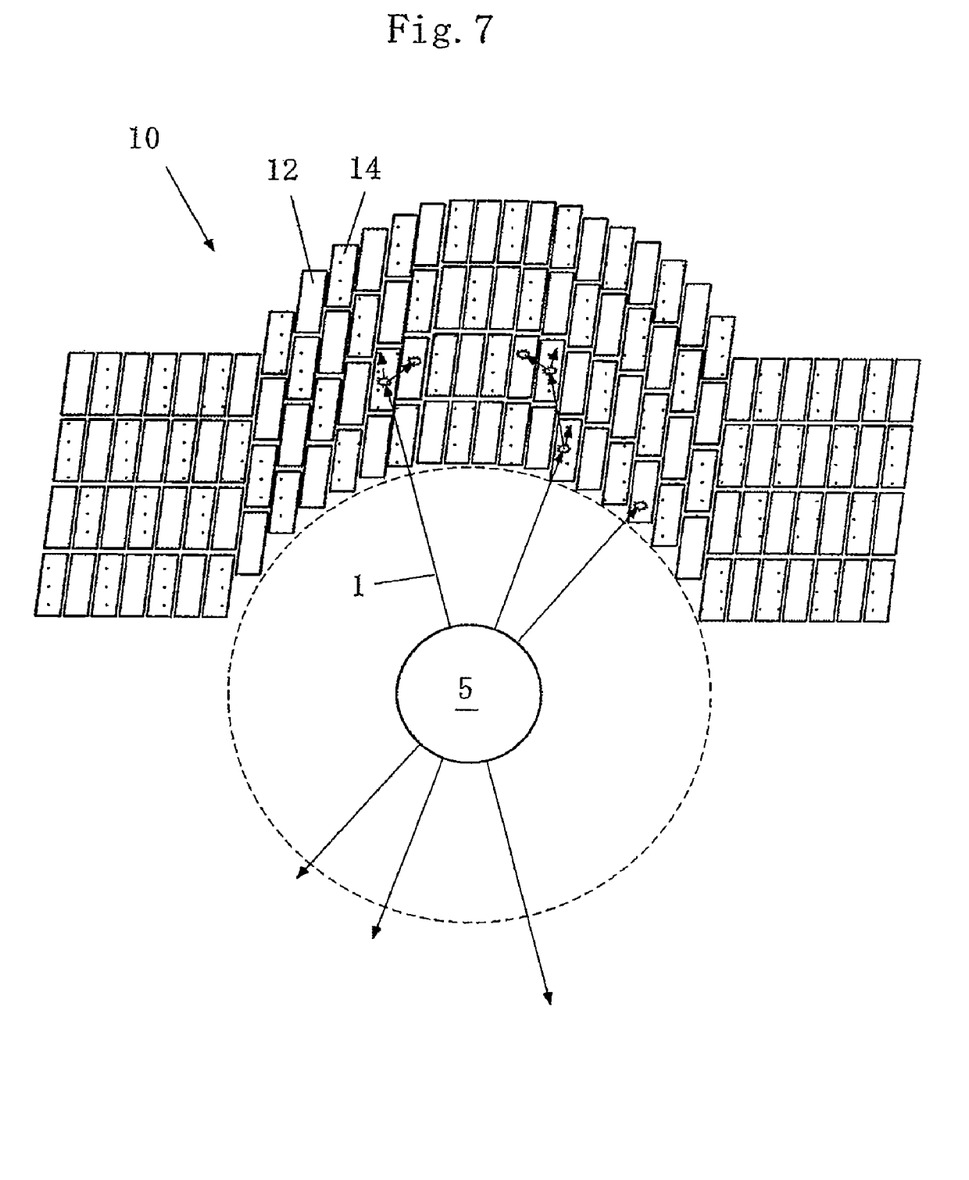
FIG. 7 is a view illustrating a modification of the detector in FIG. 6.

FIG. 7 illustrates a medical detector as a modification of the gamma ray detector in FIG. 6. In this drawing, 5 is a subject of interest (for example, the head of the human). The gamma ray detector 10 of the present invention has a layered blind-like structure (for example, four layers) and is therefore able to flexibly comply with a spherical arrangement so as to cover the human 5.

Moreover, since plastic scintillators or scintillators (organic scintillators) made from organic materials such as p-terphenyl are cheap and easy to process, it is possible to achieve a large-format practical detector and mass-production with less investment compared to the conventional NaI crystals. Development of medical detectors will be a technical breakthrough and cause a great ripple effect to take place. Furthermore, the gamma ray reconstruction method can provide the universality as the basics of radiation measurement used in various fields, for example, subnuclear physics and environmental radiation physics as well as radiation physics and medical physics.

(Fluorescence Position Calculation Method)

As a method for calculating a fluorescent source of the scintillators, a centering method described in Patent Document 2 has been used conventionally. The centering method is a method of calculating locations by obtaining the center from the ratio of light intensities obtained by detectors (for example, photomultiplier tubes) disposed on the left and right of the fluorescent screen. However, this method can obtain only the "relative position" of the light source (i.e., information on which one of the left and the right detectors has detected a fluorescence).

A new analytical method (hereinafter, referred to as "fluorescence position calculation method") for directly calculating the absolute position of the light source unlike the conventional method will be described below. This method can exhibit better performance because the mass number becomes smaller when organic scintillators (for example, plastic scintillators or p-terphenyl) which consist of molecules having a small mass number, such as carbon or hydrogen are used.

Since the organic scintillators have small mass number, the amount of light absorbed during propagation becomes very small, and hence, the distribution of light intensity obtainable from the side faces of the scintillator can be described by the cubic angle of light emitted during the fluorescence. In the case of inorganic scintillators having large mass number, it is necessary to consider influential factors such as light absorption during propagation or density distribution in the scintillator; therefore, only the case of organic scintillators will be described below.

Figure 8A:
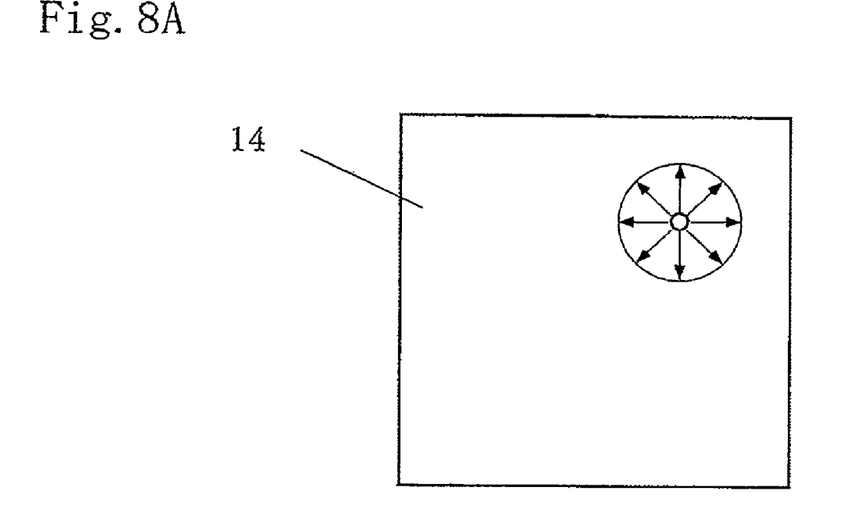
FIG. 8A is a view illustrating the propagation state of light generated on a fluorescent screen.
Figure 8B:
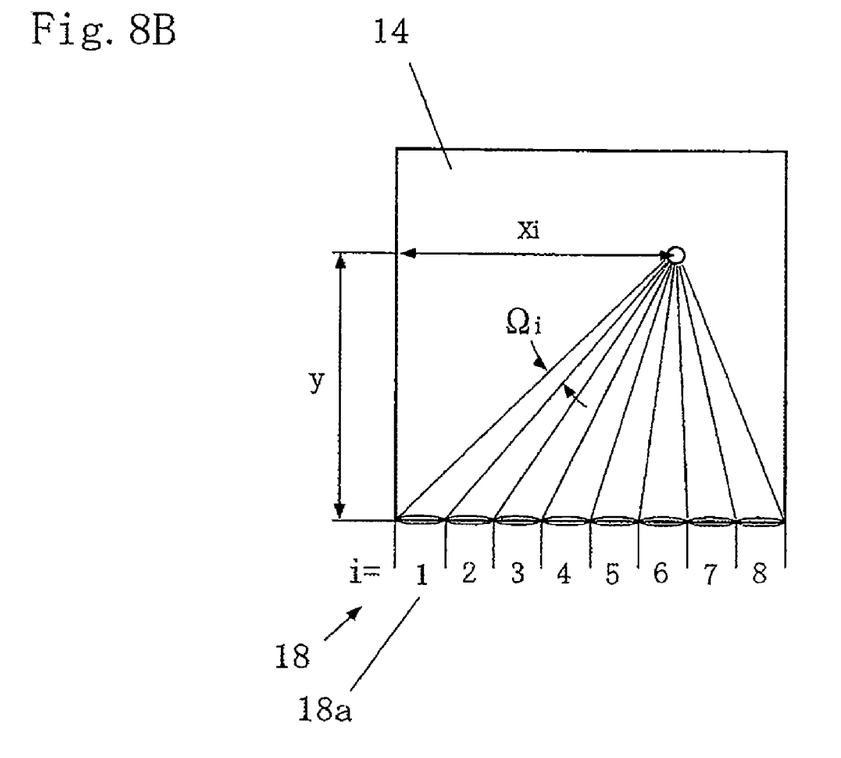
FIG. 8B is another view illustrating the propagation state of light generated on the fluorescent screen.

FIGS. 8A and 8B are views illustrating the propagation states of light generated on a fluorescent screen (Compton scattering scintillator 14). As illustrated in FIG. 8A, light emitted from the fluorescent screen is emitted omni-directionally. Moreover, as illustrated in FIG. 8B, the emitted light reaches a side face (the lower face in the drawing) while repeating total reflection.

In the present invention, in order to obtain light intensity distribution, a plurality of light intensity detectors (for example, photomultiplier tubes or a multi-anode photomultiplier tube or a semiconductor detector comprising a plurality of cells) is provided on the side face (the lower face in the drawing) of the scintillator 14 at predetermined intervals.

In FIG. 8B, although a plurality of light intensity detectors 18a is closely arranged at regular intervals on the side face of the scintillator 14, the plurality of light intensity detectors 18a may be arranged at distant position via optical intervention of optical fibers, for example. Here, i represents the number of each detector. And, $x_i$ represents the distance along the x axis from the light source to the i-th detector, and y represents the distance from the light source to the side face on which the detectors are disposed.

When the light intensity detector 18a (where detectors i of 1 to 8 are arranged at intervals of d) disposed on either side face and having a light-receiving area of a radius r is seen from the light source, the cubic angle $\Omega_i$ can be expressed by Equation (1) in Formula 1.

Here, it is to be noted that in the cubic angle of detectors disposed on the same surface, y do not depends on the location (i=1, 8) of the detectors. Moreover, $x_i$ can be expressed by Equation (2) by using the distance $x_1$ from the light source to the detector (i=1) and the distance d between detectors.

In the case of an organic scintillator having a small mass number, the light intensity $P_i$, measurable with the detector (i) can be described by a solid angle and therefore can be expressed by Equation (3). Here, A is a proportional coefficient.

By putting Equations (1), (2), and (3), the light intensity distribution obtainable on the side face can be expressed by Equation (4) using three variables (A, $X_1$, y).

By fitting this Equation (4) with respect to the light intensity distribution $P_i$ actually obtained with the detector (i=1, 8), the absolute position ($x_1$, y) of the fluorescence can be calculated.

[Formula 1]

$$\Omega_i = \frac{\pi r^2 \times y}{(x_i^2 + y^2)^{3/2}} \quad (1)$$

$$x_i = x_1 - d(i-1) \quad (2)$$

$$P_i \propto \Omega_i = A \times \Omega_i \quad (3)$$

$$P_i = A \times \frac{\pi r^2 \times y}{((x_1 - d(i-1))^2 + y^2)^{3/2}} \quad (4)$$

Since the above-described fluorescence position calculation method is able to increase the detection accuracy regardless of the detection width of the detector, it is possible to provide a positional accuracy of 1 mm or smaller with less than 10 (for example, 8) light intensity detectors even when the gamma ray incidence surface of the Compton scattering scintillator is increased (for example, 60 mm×60 mm) compared to the conventional one.

If it is possible to detect the respective emission positions in a plurality of scintillators, the incoming direction of the gamma rays can be defined 3-dimensionally by connecting the obtained emission positions together. By doing so, it is possible to identify the location of positron decay, for example, the location of cancer, occurring in the human body.

(Detection Sensitivity)

FIGS. 9A and 9B are views illustrating the reaction probabilities of gamma rays. In the drawings, the horizontal axis represents the gamma ray energy emitted from the human body, and the vertical axis represents the reaction probability per unit density.

The fluorescent screen is sodium iodide (NaI) in FIG. 9A, which is used in most radiation detectors, and a plastic scintillator is used in FIG. 9B. The bold lines represent the sum of the whole interactions, and the broken lines and the thin lines represent the absorption process and the Compton scattering process, respectively.

The detection sensitivity improvement ratio expected from the use of the above-described gamma ray reconstruction method will be described. In this invention, the detection sensitivity was compared between sodium iodide (NaI) which is generally used as a radiation detector and a plastic scintillator as the organic scintillator.

In an energy region (around 1 MeV) where energy is emitted from the human body, the reaction probability of sodium iodide which uses the absorption process was identified at point A. The reaction probability of the plastic scintillator which uses the Compton scattering was identified at point B. If they are ideal detectors, sensitivity improvements of about 20 times can be expected. Likewise, sensitivity improvements of about 5 to 10 times can be expected even when compared with other inorganic scintillators (BGO, GSO, etc.).

In accordance with the detector and method of the present invention, since the absorber scintillator 12 and the Compton scattering scintillator 14 are arranged in multiple layers so as to absorb, or Compton-scatter, the whole energy of the gamma rays 1, it is possible to absorb, or Compton-scatter, any of the gamma rays 1 in the energy range where energy is emitted from the subject.

Moreover, since the amounts of energy absorption of the gamma rays 1 simultaneously measured by the two types of scintillators 12 and 14 are combined to reconstruct the gamma rays 1, it is possible to detect and identify most of the gamma rays 1 emitted from the human body in SPECT and PET.

Therefore, the detector and method of the present invention can be used in SPECT and PET, and the detection sensitivity of the gamma rays 1 can be increased remarkably. Moreover, in cases where the gamma rays 1 exhibit a large energy distribution (e.g., the environmental radiation or the radiation emitted during radiation accidents), the whole energy can be detected and hence the identification rate of the emitted gamma rays can be increased.

As a result, the detection sensitivity can be increased and a high gamma ray identification rate can be provided. Therefore, it is possible to remarkably decrease the amount of a radioactive substance given to a subject and to remarkably reduce the amount of radiation exposure.

As described above, in accordance with the detector and method of the present invention, a medical radiation detector for early disease diagnosis can be achieved with very high resolution, thus improving imaging diagnosis technologies and achieving a reduction in the measurement time needed for measuring radiation emitted from the human body and a reduction in the dose of medication (low exposure) to the human body.

The present invention is not limited to the above-described embodiment but various modifications can be made without departing from the gist of the present invention.

The invention claimed is:

1. A gamma ray detector comprising:
   (a) a plurality of absorber scintillators made from an absorptive substance exhibiting substantial absorption with respect to gamma rays in an energy region, emitted from a subject;
   (b) a plurality of Compton scattering scintillators made from a Compton scattering substance exhibiting a substantial probability of Compton scattering with respect to the gamma rays; and
   (c) an energy detector that combines the amounts of gamma ray energy absorption simultaneously measured by a first absorber scintillator and a first Compton scattering scintillator to reconstruct gamma rays emitted from the subject,
   wherein the absorber scintillators and the Compton scattering scintillators are arranged in multiple layers and alternately or randomly in an identical surface and in a direction of lamination so as to absorb, or Compton-scatter, the whole energy of the gamma rays.

2. The gamma ray detector according to claim 1, wherein the Compton scattering substance is an organic material having a small mass number, consisting of carbon molecules and hydrogen molecules.

3. The gamma ray detector according to claim 1, wherein the energy detector comprises
   an absorption light intensity detector that is optically coupled to the first absorber scintillator so as to detect light intensity of the first absorber scintillator;
   a Compton scattering light intensity detector that is optically coupled to the first Compton scattering scintillator so as to detect light intensity of the first Compton scattering scintillator; and
   a calculator that calculates the amount of energy associated with an identical gamma ray from the respective light intensities.

4. The gamma ray detector according to claim 3,
   wherein the Compton scattering light intensity detector comprises a plurality of light intensity detectors that is optically arranged at predetermined intervals on a predetermined surface of the first Compton scattering scintillator, and
   wherein the calculator calculates the incident positions of the gamma rays from the light intensity distribution of the plurality of light intensity detectors.

5. The gamma ray detector according to claim 1, wherein the absorptive substance is NaI.

6. The gamma ray detector according to claim 1, wherein the Compton scattering substance is an organic material comprising p-terphenyl.

7. A gamma ray reconstruction method comprising the steps of:
   (a) arranging a plurality of absorber scintillators and a plurality of Compton scattering scintillators in multiple layers and alternately or randomly in an identical surface and in a direction of lamination so as to absorb, or Compton-scatter, the energy of gamma rays,
   wherein the absorber scintillators are made from an absorptive substance exhibiting a substantial absorption with respect to the gamma rays in an energy region, emitted from a subject, and the Compton scattering scintillators are made from a Compton scattering substance exhibiting a substantial probability of Compton scattering with respect to the gamma rays; and
   (b) combining the amounts of gamma ray energy absorption simultaneously measured by the absorber scintillators and the Compton scattering scintillators to reconstruct the gamma rays emitted from the subject.

8. The gamma ray reconstruction method according to claim 7, wherein a plurality of light intensity detectors is optically arranged on a predetermined surface of a first Compton scattering scintillator so as to calculate the incident positions of the gamma rays from the light intensity distribution of the plurality of light intensity detectors.

9. The gamma ray reconstruction method according to claim 7, wherein the absorptive substance is NaI.

10. The gamma ray reconstruction method according to claim 7, wherein the Compton scattering substance is an organic material comprising p-terphenyl.

* * * * *